(12) United States Patent
Sugita et al.

(10) Patent No.: US 7,699,836 B2
(45) Date of Patent: Apr. 20, 2010

(54) TREATMENT TOOL FOR ENDOSCOPE

(75) Inventors: Noriyuki Sugita, Saitama (JP); Satoshi Kidooka, Saitama (JP)

(73) Assignee: Hoya Corporation, Tokyo (JP)

( * ) Notice: Subject to any disclaimer, the term of this patent is extended or adjusted under 35 U.S.C. 154(b) by 1108 days.

(21) Appl. No.: 11/349,084

(22) Filed: Feb. 8, 2006

(65) Prior Publication Data
US 2006/0178657 A1 Aug. 10, 2006

(30) Foreign Application Priority Data
Feb. 9, 2005 (JP) .............................. 2005-032960

(51) Int. Cl.
*A61B 17/00* (2006.01)
(52) U.S. Cl. ........................... 606/1; 600/101; 600/104; 600/106; 600/107
(58) Field of Classification Search ........................ None
See application file for complete search history.

(56) References Cited

U.S. PATENT DOCUMENTS

| | | | | |
|---|---|---|---|---|
| 1,901,731 | A * | 3/1933 | Buerger | 600/107 |
| 2,031,020 | A * | 2/1936 | Wappler | 606/46 |
| 3,924,608 | A * | 12/1975 | Mitsui | 600/107 |
| 4,224,929 | A * | 9/1980 | Furihata | 600/116 |
| 4,452,236 | A * | 6/1984 | Utsugi | 600/107 |
| 5,658,302 | A * | 8/1997 | Wicherski et al. | 606/159 |
| 6,015,381 | A | 1/2000 | Ouchi | |
| 6,210,398 | B1 | 4/2001 | Ouchi | |
| 6,261,284 | B1 | 7/2001 | Ouchi | |
| 6,352,503 | B1 | 3/2002 | Matsui et al. | |
| 6,458,074 | B1 | 10/2002 | Matsui et al. | |
| 2002/0091303 | A1* | 7/2002 | Ootawara et al. | 600/106 |
| 2005/0215996 | A1 | 9/2005 | Ouchi | |
| 2008/0287825 | A1* | 11/2008 | Cooke | 600/562 |

FOREIGN PATENT DOCUMENTS

| | | |
|---|---|---|
| JP | 9-262239 | 10/1997 |
| JP | 10-165359 | 6/1998 |
| JP | 11-042232 | 2/1999 |
| JP | 2000-037348 | 2/2000 |
| JP | 3679674 | 5/2005 |

OTHER PUBLICATIONS

English Language Abstract of JP 9-262239.
English Language Abstract of JP 10-165359.
English Language Abstract of JP 11-042232.
English Language Abstract of JP 2000-037348.
U.S. Appl. No. 11/344,079 to Shibata, filed Feb. 1, 2006.
U.S. Appl. No. 11/349,083 to Sugita et al., filed Feb. 8, 2006.

* cited by examiner

*Primary Examiner*—Henry M Johnson, III
*Assistant Examiner*—Lynsey Crandall
(74) *Attorney, Agent, or Firm*—Greenblum & Bernstein P.L.C.

(57) ABSTRACT

A treatment tool for an endoscope, having a flexible sheath being made of electrically insulating material to be inserted through an instrument channel of the endoscope, an operation wire, which is adapted to be advanced and retracted in an axial direction of the sheath inside the sheath, a treatment instrument, which is arranged at a distal portion of the treatment tool and is adapted to be protruded and retracted from a distal end of the sheath, and a fluid channel with an opening, through which fluid is ejected toward the treatment instrument, is provided. The operation wire and the fluid channel are arranged inside the sheath in parallel with an axis of the sheath. The treatment instrument is connected to the operation wire in a laterally displaced position with respect to the operation wire, and is arranged in front of the opening of the fluid channel.

6 Claims, 8 Drawing Sheets

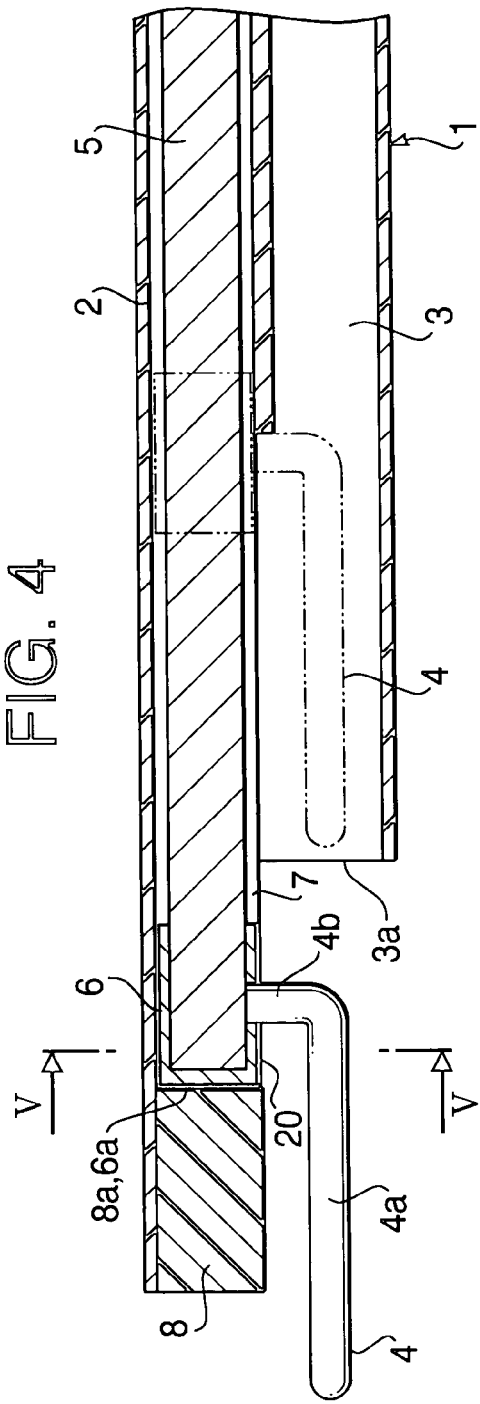
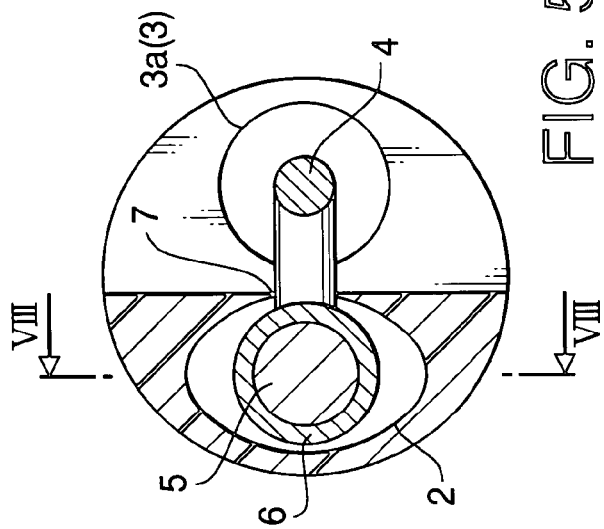

TREATMENT TOOL FOR ENDOSCOPE

BACKGROUND OF THE INVENTION

The present invention relates to a treatment tool for an endoscope.

Conventionally, various types of treatment tools for endoscopes have been provided, including a tip portion as a treatment instrument that is adapted to be protruded and retracted from a tip end of a sheath being inserted through an instrument channel of the endoscope. The tip portion is protruded and retracted by advancing and retracting an operation wire arranged in the sheath in an axial direction thereof.

Such a treatment tool is generally provided with a fluid channel to convey water forwardly therethrough to a distal end of the treatment tool so that the tip portion with in vivo tissues such as mucous membranes is cleaned, and an example of such a treatment tool is disclosed in Japanese Patent Provisional Publication No. HEI10-165359.

The above referenced treatment instrument is provided with a fluid channel independently from an operation wire, however, such a treatment tool may use an inner tube, in which the operation wire is arranged, as the fluid channel to convey water therethrough.

When the treatment tool is provided with the independent fluid channel, a distal opening of the fluid channel is arranged in an offset position with respect to a diameter of an outer tube. Due to the offset position of the opening, a front portion of the treatment instrument with mucous membranes stained, which is most often required to be cleaned, may not be washed substantially with the ejected water.

When the treatment tool uses the inner tube as the fluid channel, the opening is arranged in the center of the diameter, therefore the front portion of the treatment instrument may be washed. However, the fluid channel, which is partially occupied by the operation wire, may not be capable of delivering enough water.

It should be noted that the above referenced treatment tool is not provided with a bending mechanism to control an orientation of the treatment instrument in an arbitrary direction by a remote operation from a user, however, such a mechanism is desirable to have the treatment instrument lead in a targeted area for the treatment.

Japanese Patent Provisional Publications No. HEI9-262239 and No. HEI11-42232 disclose treatment tools with such bending mechanisms. However, tip portions of these treatment tools are not configured to be protruded and retracted from distal ends of sheaths. Further, such treatment tools are required to have additional operation wires to bend distal portions inside the sheaths, which make the structures the operations of the treatment tools complicated.

SUMMARY OF THE INVENTION

The present invention is advantageous in that a treatment tool for an endoscope capable of cleaning a tip front portion thereof effectively with substantial quantity of fluid in a less complicated structure is provided. Further, the tip portion of the treatment tool can be controlled to be oriented in an arbitrary direction in a simple operation.

According to an aspect of the present invention, a treatment tool for an endoscope, having a flexible sheath being made of electrically insulating material to be inserted through an instrument channel of the endoscope, an operation wire, which is adapted to be advanced and retracted in an axial direction of the sheath inside the sheath, a treatment instrument, which is arranged at a distal portion of the treatment tool and is adapted to be protruded and retracted from a distal end of the sheath, and a fluid channel with an opening, through which fluid is ejected toward the treatment instrument, is provided. The operation wire and the fluid channel are arranged inside the sheath in parallel with an axis of the sheath. The treatment instrument is connected to the operation wire in a laterally displaced position with respect to the operation wire, and is arranged in front of the opening of the fluid channel.

Optionally, a distal portion of the sheath may be formed to be hemi-cylindrical, and a hemi-cylindrical portion of the sheath on which the fluid channel may be formed is partially cut off at the distal portion of the sheath.

Optionally, the treatment instrument may include a base portion and an elongated portion. A distal portion of the sheath may be provided with a slit, in which the base portion of the treatment instrument is adapted be slidable in parallel with the axis of the sheath.

Optionally, the operation wire may be connected to the treatment instrument via a connecting member having a distal surface. The sheath may be provided with a stopper surface at the distal end thereof. The stopper surface may be inclined with respect to the distal surface of the connecting member when the connecting member is installed in the sheath. An orientation of the treatment instrument may be changed correspondingly to the inclination of the stopper surface by having the distal surface of the connecting member pressed against the stopper surface when the operation wire is pressed from a proximal end of the sheath toward the distal end of the sheath.

Optionally, a cross-sectional area of a channel in which the operation wire is arranged may be formed to have an elongated shape in parallel with a plane, in which the orientation of the treatment instrument is changed, at least at a distal portion of the sheath so that the operation wire can be deformed therein.

BRIEF DESCRIPTION OF THE DRAWINGS

FIG. 4 is a cross-sectional side view of a distal portion of the treatment tool according to the embodiment of the invention.

FIG. 5 shows a cross-sectional view of the distal portion of the treatment tool taken along the line V-V in FIG. 4 according to the embodiment of the invention.

DETAILED DESCRIPTION OF THE EMBODIMENTS

Hereinafter, referring to the accompanying drawings, a treatment tool according to an illustrative embodiment of the invention will be described.

Figure 2:
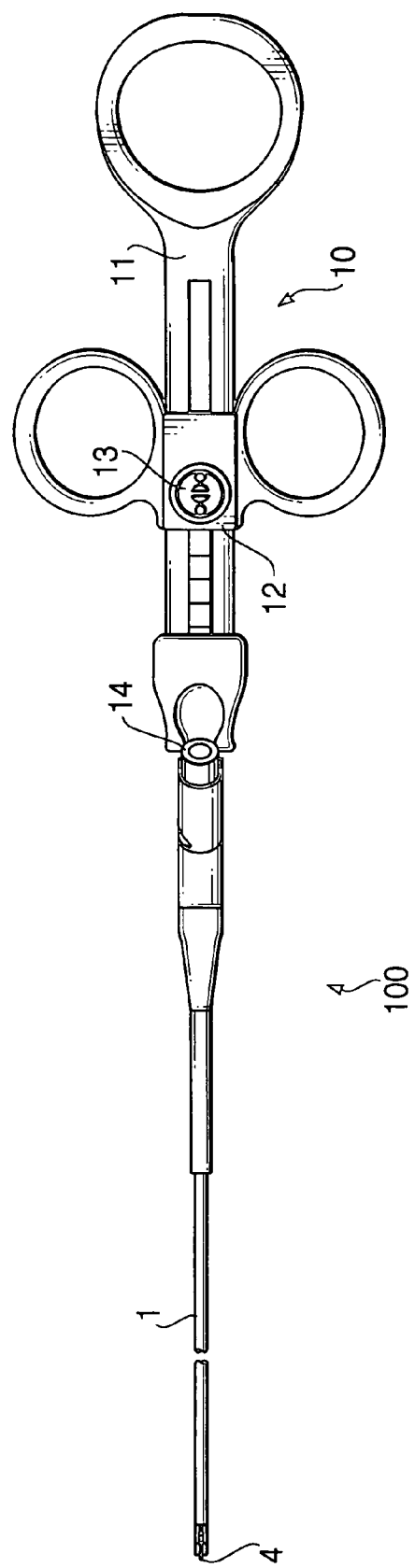
FIG. 2 shows a plane view of an entire configuration of the treatment tool according to the embodiment of the invention.
Figure 3:
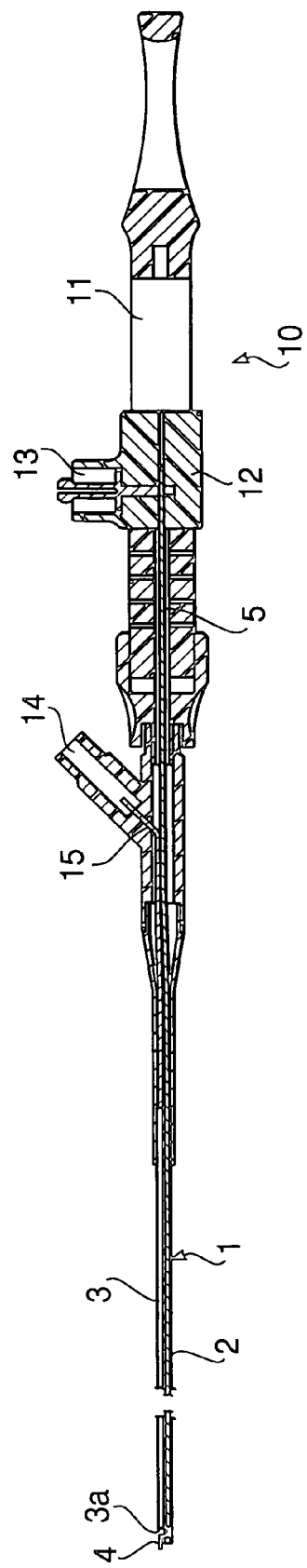
FIG. 3 shows a cross-sectional side view of the entire configuration of the treatment tool according to the embodiment of the invention.

FIG. 2 shows a plane view of an entire configuration of the treatment tool 100 for an endoscope according to the embodiment of the invention. FIG. 3 shows a cross-sectional side view of the entire configuration of the treatment tool according to the embodiment of the invention.

The treatment tool 100 includes a flexible tubular sheath 1, which is made of an electrically insulated material, for example polytetrafluoroethylene, and has a length ranging for example from one to two meters. The sheath 1 is adapted to be inserted through an instrument channel (not shown) of the endoscope.

The sheath 1 is formed to be a multi-lumen tube having a plurality of (for example, two) independent lumens, which are a wire lumen 2 and a fluid channel 3, formed in parallel with each other through the entire length of the sheath 1. It should be noted, however, that the sheath 1 may not necessarily have more than one lumens, but may be formed as a single-lumen tube.

At a distal portion of the sheath 1, a rod-like high-frequency electrode 4 as a treatment instrument is provided, and is configured to be protruded outwardly and retracted inwardly by an operation from a user via an operation unit 10, which is provided at a proximal end of the sheath 10.

Further, an operation wire 5 (which is a electrically conductive wire made of, for example, one of stainless steel) is inserted over an entire length of the sheath 1. The operation wire 5 is movable along an axis of the sheath 1 (i.e., in the axial direction of the sheath 1), and the electrode 4 is connected to a distal end of the operation wire 5.

The operation unit 10 includes an operation shaft 11, which is connected to the proximal end of the sheath 1, and a slidable portion 12, which is adapted to slide along the axial direction of the operation unit 10. The slidable portion 12 is connected with a proximal end of the operation wire 5. With this configuration, the electrode 4 can be protruded and retracted from the distal portion of the sheath 1 by the operation from the user.

The slidable portion 12 is provided with a terminal 13, to which a power supplying cable (not shown) is connected, so that electrical current with high-frequency can be supplied to the operation wire 5.

The high-frequency treatment tool 100 is further provided with a fluid filler port 14, which is in communication with the water channel 3 via a connecting tube 15. From the fluid filler port 14 with an injection tool (not shown) installed, fluid such as water is injected into the fluid channel 3 and is advanced to be ejected from an opening 3a provided at the distal end of the sheath 1.

Figure 6:
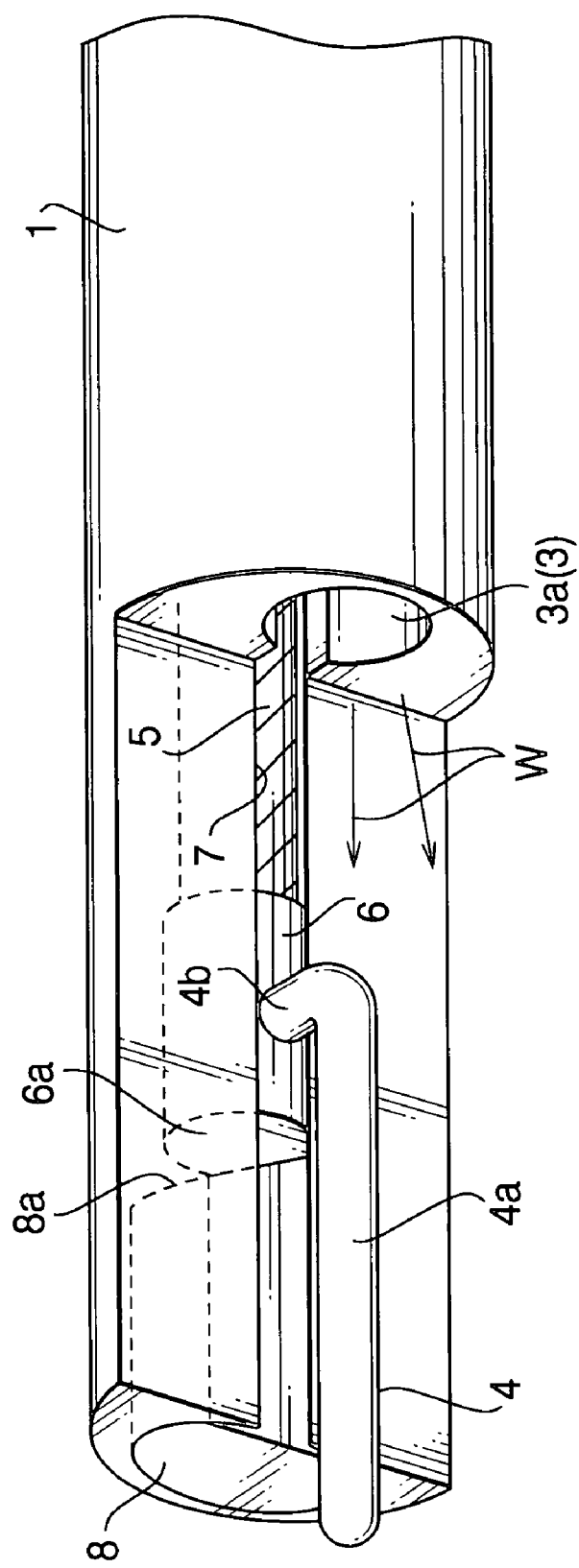
FIG. 6 shows a perspective view of the distal portion of the treatment tool according to the embodiment of the invention.

FIG. 4 is a cross-sectional side view of the distal portion of the treatment tool 100 according to the embodiment of the invention. FIG. 5 shows a cross-sectional view of the distal portion of the treatment tool 100 taken along the line V-V in FIG. 4 according to the embodiment of the invention. FIG. 6 shows a perspective view of the distal portion of the treatment tool 100 according to the embodiment of the invention.

As shown in FIGS. 4 through 6, the distal portion of the sheath 1 is formed to be hemi-cylindrical, and a hemi-cylindrical portion of the distal portion that is in for example approximately one centimeter from the distal end of the sheath 1 in the axial direction is cut off in parallel with a diameter of the sheath 1. The opening 3a of the fluid channel 3 is provided on a cross-sectional surface of the cutoff portion, which is retracted for the approximately one centimeter from the distal end of the sheath 1.

The electrode 4, made of electrically conductive metal, is formed to have a shape of an L, and is fixed to a side of a connecting member 6 at a proximal end thereof. The connecting member 6 is made of electrically conductive metal, and is fixed to a distal end of the operation wire 5. The electrode 4 has an elongated portion 4a, which is in a laterally displaced position extended in parallel with the axial direction of the sheath 1, and a base portion 4b, which is adapted to be slidably moved in a slit 7. The electrode is formed to be protruded from a side surface 20 of the distal portion, which is formed by having the hemi-cylindrical portion of the distal portion cut off from the sheath 1.

Figure 7:
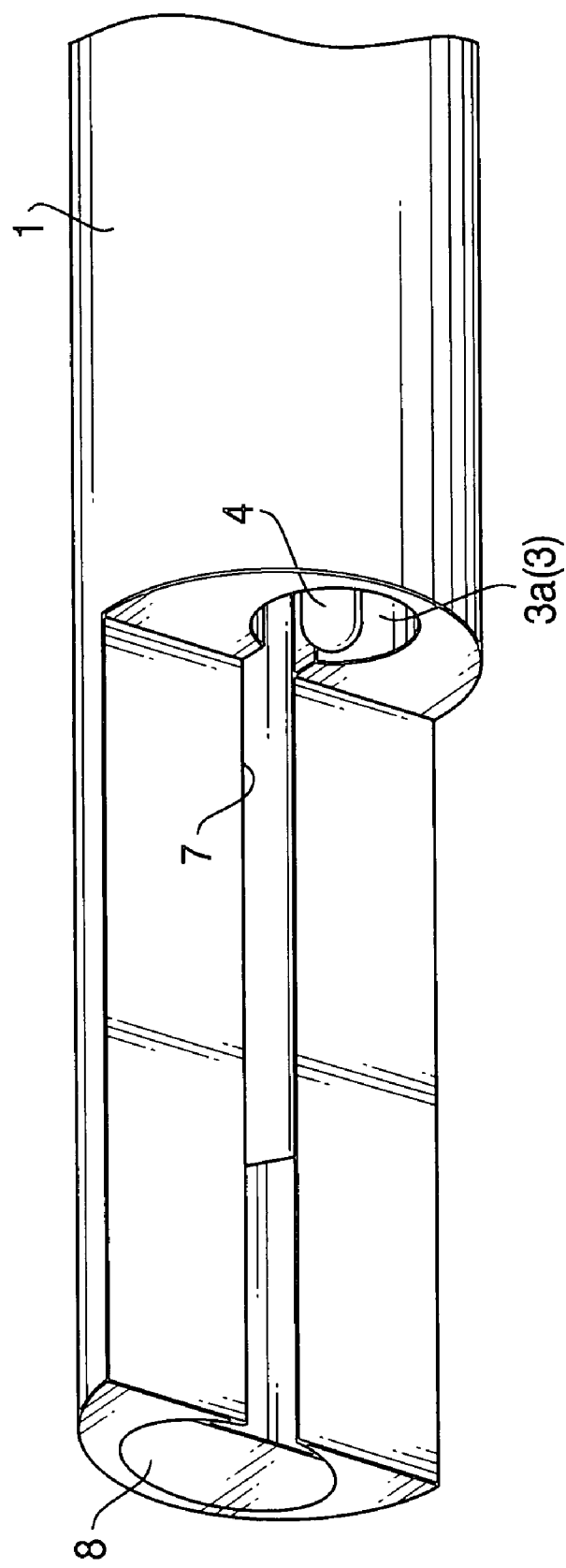
FIG. 7 shows a perspective view of the tip portion of the treatment tool with a high-frequency electrode being retracted in a sheath according to the embodiment of the invention.

The slit 7 is formed in parallel with the axial direction of the sheath 1 on a wall that separates the wire lumen 2 and the fluid channel 3, and extends on the side surface 20 of the distal portion. When the operation wire 5 is retracted by the user toward the operation unit 10, the electrode 4 is retracted and included in a distal portion of the fluid channel 3, as shown in the dotted line in FIG. 4. FIG. 7 shows a perspective view of the tip portion of the treatment tool 100 with the electrode 4 being retracted in a sheath 1 according to the embodiment of the invention.

The sheath 1 is further provided with a stopper member 8, which is made of an electrically insulated material, at a distal end of the wire lumen 2, so that a front surface 6a of the connecting member 6 is in contact with a rear surface 8a of the stopper member 8, and the connecting member 6 is prevented from being further advanced.

When the operation wire 5 is advanced via the operation unit 10 toward the distal end of the sheath 1, the electrode 4 is advanced and exposed through the opening 3a, and a distal end of the electrode 4 is protruded from the distal end of the sheath 1. When the operation wire 5 is further advanced, the front surface 6a of the connecting member 6 is in contact with the rear surface 8a of the stopper member 8, and the operation wire 5 and the electrode 4 are stopped. Thus, the electrode 4 is protruded and retracted from the distal end of the sheath 1 by a remote operation of the user.

When the electrode 4 is cleaned, fluid is injected through the fluid filler port 14, and the fluid is ejected from the opening 3a of the fluid channel 3 toward the electrode 4 as indicated by the arrows W in FIG. 6, so that the distal end of the electrode is washed.

With the above described configuration, the electrode 4 with mucous membranes is effectively cleaned with substantial quantity of fluid, as the fluid channel 3 is provided independently from the operation wire 5.

Figure 8:
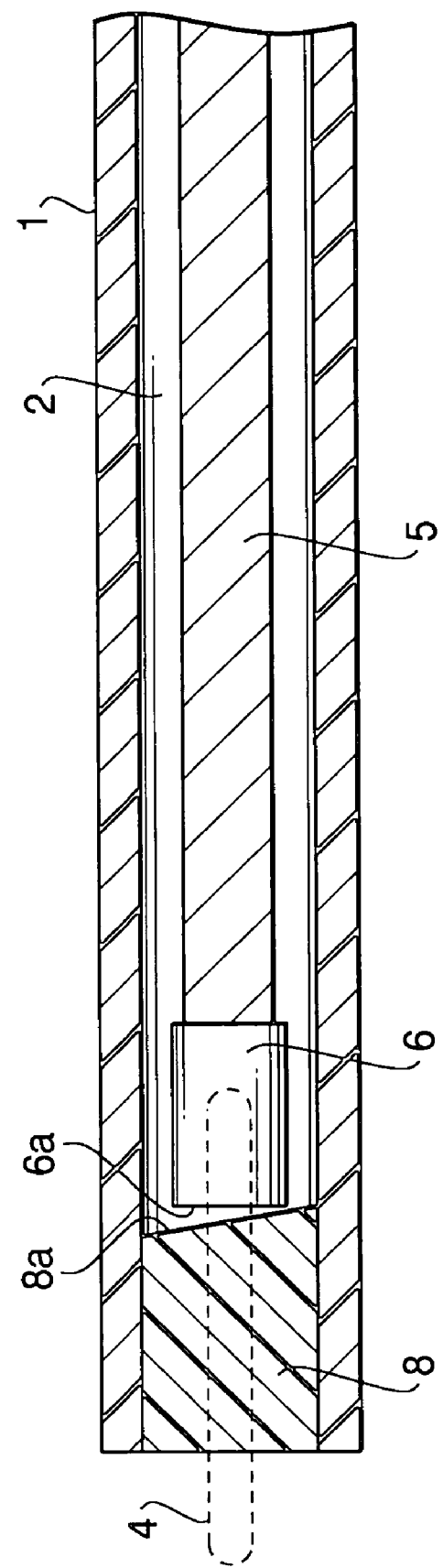
FIG. 8 shows a cross-sectional side view of the tip portion of the treatment tool taken along the line VIII-VIII in FIG. 5 according to the embodiment of the invention.

FIG. 8 shows a cross-sectional side view of the tip portion of the treatment tool 100 taken along the line VIII-VIII in FIG. 5 according to the embodiment of the invention. The rear surface 8a of the stopper member 8 is formed to be inclined with respect to the axis of the sheath 1, while the front surface 6a of the connecting member 6 is formed to be perpendicular to the axis of the sheath 1. Therefore, the rear surface 8a is formed to be inclined with respect to the front surface 6a.

Figure 1:
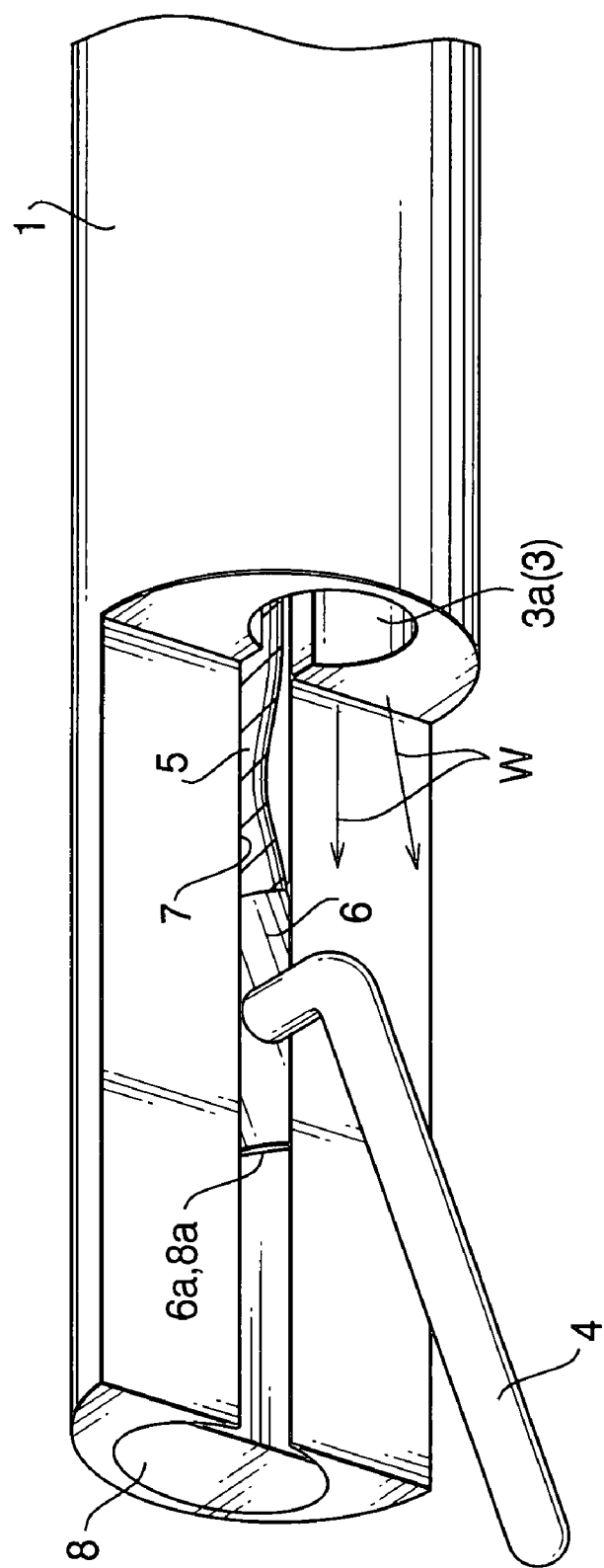
FIG. 1 is a partially exploded perspective view of a treatment tool according to an embodiment of the invention.
Figure 9:
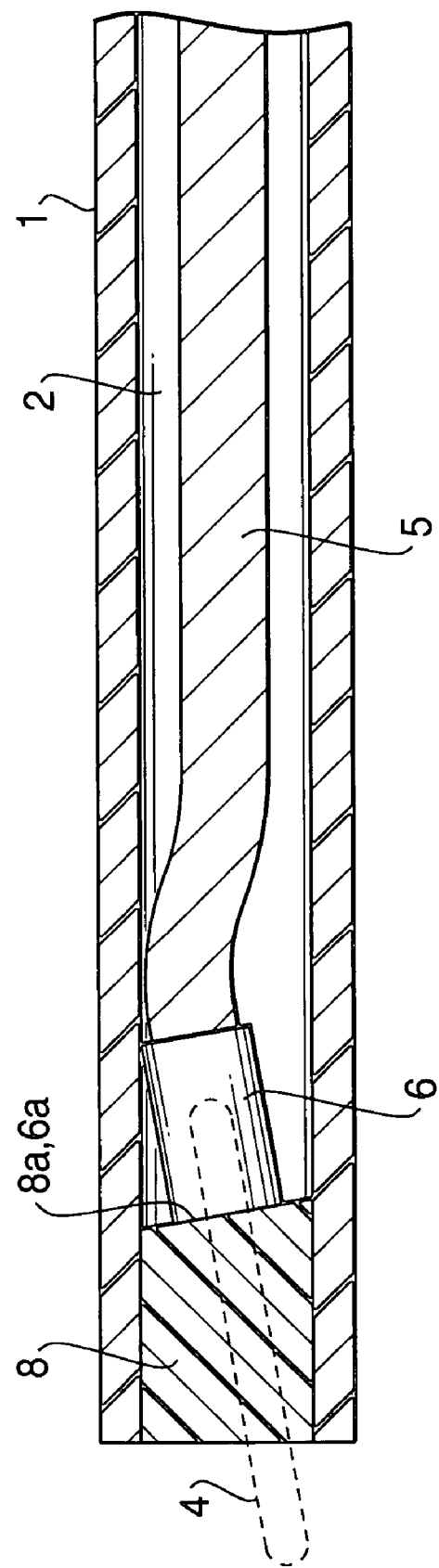
FIG. 9 shows a cross-sectional side view of the treatment tool with the high-frequency electrode biased at an angle according to the variation of the second embodiment of the invention.

With this configuration, when the operation wire 5 is further pressed toward the distal end of the sheath 1 from the position indicated in FIG. 8 and the front surface 6a of the connecting member 6 is pressed against the stopper member 8, the connecting member 6 is turned at a small angle so that an entire area of the front surface 6a is in contact with the rear surface 8a, as shown in FIG. 9. Accordingly, the distal portion of the operation wire 5 that is in connection with the connecting member 6 is curved, and the electrode 4 that is also in connection with the connecting member 6 is biased, as shown in FIG. 1.

The orientation of the electrode 4 returns to the initial orientation, which is in parallel with the axial direction of the sheath 1, when the connecting member 6 is released from the pressing force. Thus, the orientation of the electrode 4 can be arbitrarily changed with the operation to the operation wire 5 that can be also used to for protruding and retracting the electrode 4. It should be noted that a cross-sectional area of the wire lumen 2 is formed to have an elongated shape, for example an oval, at least at the distal portion of the sheath 1, so that the operation wire 5 has space to be deformed therein.

Although an example of carrying out the invention have been described above, the present invention is not limited to the above described embodiments. For example, in the above described embodiment, the rear surface 8a of the stopper member 8 is formed to be inclined, however, the front surface 6a of the connecting member 6 may be formed to be inclined and the rear surface 8a may be formed to be perpendicular to the axis of the sheath 1. Further, the stopper member 8 may be formed integrally with the sheath 1. It should be further noted that the present invention may be applied to a treatment tool that is not supplied with high-frequency electrical current.

The present disclosure relates to the subject matter contained in Japanese Patent Application No. 2005-032960, filed on Feb. 9, 2005, which is expressly incorporated herein by reference in its entirety.

What is claimed is:

1. A treatment tool for an endoscope, comprising:
   a flexible sheath being made of electrically insulating material to be inserted through an instrument channel of the endoscope,
   an operation wire, which is adapted to be advanced and retracted in an axial direction of the sheath inside the sheath,
   a treatment instrument, which is arranged at a distal portion of the treatment tool and is adapted to be protruded and retracted from a distal end of the sheath, and
   a fluid channel with an opening, through which fluid is ejected toward the treatment instrument,
   wherein the operation wire and the fluid channel are arranged inside the sheath in parallel with an axis of the sheath,
   wherein the treatment instrument is connected to the operation wire in a laterally displaced position with respect to the operation wire, and is arranged in front of the opening of the fluid channel;
   wherein the operation wire is connected to the treatment instrument via a connecting member having a distal surface,
   wherein the sheath is provided with a stopper surface at the distal end thereof, the stopper surface being inclined with respect to the distal surface of the connecting member when the connecting member is installed in the sheath,
   wherein an orientation of the treatment instrument is changed correspondingly to the inclination of the stopper surface by having the distal surface of the connecting member pressed against the stopper surface when the operation wire is pressed from a proximal end of the sheath toward the distal end of the sheath.

2. The treatment tool according to claim 1, wherein a distal portion of the sheath is formed to be hemi-cylindrical, and a hemi-cylindrical portion of the sheath on which the fluid channel is formed is partially cut off at the distal portion of the sheath.

3. The treatment tool according to claim 1,
   wherein the treatment instrument includes a base portion and an elongated portion, and
   wherein a distal portion of the sheath is provided with a slit, in which the base portion of the treatment instrument is adapted to be slidable in parallel with the axis of the sheath.

4. The treatment tool according to claim 1, wherein a cross-sectional area of a channel, in which the operation wire is arranged, is formed to have an elongated shape in parallel with a plane, in which the orientation of the treatment instrument is changed, at least at a distal portion of the sheath so that the operation wire can be deformed therein.

5. The treatment tool according to claim 2,
   wherein the treatment instrument includes a base portion and an elongated portion,
   wherein the distal portion of the sheath is provided with a slit, in which the base portion of the treatment instrument is adapted to be slidable in parallel with the axis of the sheath.

6. The treatment tool according to claim 5, wherein a cross-sectional area of a channel, in which the operation wire is arranged, is formed to have an elongated shape in parallel with a plane, in which the orientation of the treatment instrument is changed, at least at a distal portion of the sheath so that the operation wire can be deformed therein.

* * * * *